US009655945B2

(12) United States Patent
Angeli et al.

(10) Patent No.: US 9,655,945 B2
(45) Date of Patent: May 23, 2017

(54) TREATMENT OF ASCITES

(71) Applicants: NanoAntibiotics, Inc., Beverly, MA (US); Universita degli Studi di Padova, Padua (IT)

(72) Inventors: Paolo Angeli, Padua (IT); Penelope Markham, Clifton, VA (US); Jonathan Adams, Chicago, IL (US)

(73) Assignee: BIOVIE, Inc., Beverly, MA (US)

( * ) Notice: Subject to any disclaimer, the term of this patent is extended or adjusted under 35 U.S.C. 154(b) by 0 days.

(21) Appl. No.: 15/198,050

(22) Filed: Jun. 30, 2016

(65) Prior Publication Data
US 2017/0000844 A1  Jan. 5, 2017

Related U.S. Application Data

(60) Provisional application No. 62/186,638, filed on Jun. 30, 2015, provisional application No. 62/267,510, filed on Dec. 15, 2015, provisional application No. 62/321,558, filed on Apr. 12, 2016.

(51) Int. Cl.
*A61K 38/11* (2006.01)

(52) U.S. Cl.
CPC .................... *A61K 38/11* (2013.01)

(58) Field of Classification Search
CPC ..................................... A61K 38/11
See application file for complete search history.

(56) References Cited

U.S. PATENT DOCUMENTS

| | | | | |
|---|---|---|---|---|
| 7,160,853 B2 * | 1/2007 | Lebrec | | A61K 38/11 514/15.3 |
| 2004/0102362 A1 * | 5/2004 | Lebrec | | A61K 38/11 514/1.1 |
| 2011/0237494 A1 * | 9/2011 | Laporte | | A61K 38/12 514/1.4 |
| 2011/0300109 A1 | 12/2011 | Tepic et al. | | |
| 2012/0157526 A1 * | 6/2012 | Jalan | | A61K 31/19 514/555 |
| 2014/0147875 A1 | 5/2014 | Everson et al. | | |
| 2014/0378660 A1 * | 12/2014 | Short | | G01N 33/6845 530/350 |
| 2015/0056194 A1 | 2/2015 | Hsu | | |
| 2015/0126432 A1 | 5/2015 | Wisniewski et al. | | |

FOREIGN PATENT DOCUMENTS

WO  WO 2013/106072  7/2013

OTHER PUBLICATIONS

Alessandria et al., "Renal failure in cirrhotic patients: role of terlipressin in clinical approach to hepatorenal syndrome type 2," European Journal of Gastroenterology & Hepatology, 2002, pp. 1362-1368, vol. 14.

Alessandria et al., "Noradrenalin vs terlipressin in patients with hepatorenal syndrome: A prospective, randomized, unblinded, pilot study," Journal of Hepatology, 2007, pp. 499-505, vol. 47.

Ali et al., "Clinical Study on the Therapeutic Role of Midodrine in Non azotemic Cirrhotic Patients with Tense Ascites: A Double-Blind, Placebo-Controlled, Randomized Trial," Hepato-Gastroenterology, 2014, pp. 1915-1925, vol. 61.

Angeli et al., "Hyponatremia in Cirrhosis: Results of a Patient Population Survey," Hepatology, 2006, pp. 1525-1542, vol. 44.

Angeli et al. "Terlipressin given as continuous intravenous infusion is the more suitable schedule for the treatment of type 1 hepatorenal syndrome (HRS) in patients with cirrhosis: results of a controlled clinical study," Journal of Heptology, Abstract 175 of the 44th Annual Meeting of the European Association for the Study, 2009, vol. 50, Supplement 1.

Angeli , P., "Terlipressin for Hepatorenal Syndrome: Novel Strategies and Future Perspectives," Ascites, Hyponatremia and Hepatorenal Syndrome: Progress in Treatment, 2011, pp. 189-197, vol. 28.

Bari et al., "The Combination of Octreotide and Midodrine Is Not Superior to Albumin in Preventing Recurrence of Ascites After Large-Volume Paracentesis," Clinical Gastroenterology and Hepatology, 2012, pp. 1169-1175, vol. 10.

Caraceni et al., "Long-term treatment of hepatorenal syndrome as a bridge to liver transplantation," Digestive and Liver Disease, 2011, pp. 242-245, vol. 43.

Cavallin et al., "Terlipressin plus albumin versus midodrine and octreotide plus albumin in the treatment of hepatorenal syndrome: a randomized trial," Hepatology, 2015, pp. 567-574, vol. 62, No. 2.

Cavallin et al., "Terlipressin Given by Continuous Intravenous Infusion Versus Intravenous Boluses in the Treatment of Hepatroenal Syndrome: A Randomized Controlled Study," Hepatology, 2016, pp. 983-992, vol. 63, No. 3.

Cervoni, M.D., Jean Paul et al., "Terlipressin May Influence the Outcome of Hepatorenal Syndrome Complicating Alcoholic Hepatitis," Am. J. Gastroenterol., 1997, pp. 2113-2114, vol. 92, No. 11.

Ding et al., "Hemodynamic effects of continuous versus bolus infusion of terlipressin for portal hypertension: A randomized comparison," Gastroenterology and Hepatology, 2013, pp. 1242-1246, vol. 28.

Döhler, Klaus D., "Terlipressin and Hyponatremia," A short review, Curatis Pharma GmbH, Oct. 31, 2010, 6 pages.

Fabrizi et al., "Terlipressin for hepatorenal syndrome: A meta-analysis of randomized trials," The International Journal of Artificial Organs, 2009, pp. 133-140, vol. 32, No. 3.

Fernández-Varo et al., "Vasopressin 1a Receptor Partial Agonism Increases Sodium Excretion and Reduces Portal Hypertension and Ascites in Cirrhotic Rats," Hepatology, 2016, pp. 207-216, vol. 63, No. 1.

(Continued)

*Primary Examiner* — Amber D Steele
(74) *Attorney, Agent, or Firm* — McDonnell Boehnen Hulbert & Berghoff LLP

(57) ABSTRACT

A method for treating ascites patients by administering the peptide drug terlipressin by continuous infusion. The patients include those whose ascites condition has not progressed to hepatorenal syndrome (HRS). Administration may be accomplished with a continuous infusion pump.

14 Claims, No Drawings

(56) References Cited

OTHER PUBLICATIONS

Fiamiani et al., "The use of terlipressin in cirrhotic patients with refractory ascites and normal renal function: A multicentric study," European Journal of Internal Medicine, 2011, pp. 587-590, vol. 22.
Gadano et al., "Natriuretic response to the combination of atrial natriuretic peptide and terlipressin in patients with cirrhosis and refractory ascites," Journal of Hepatology, 1997, pp. 1229-1234, vol. 26.
Ganne-Carrié, M.D., Nathalie et al., "Hepatorenal Syndrome Long-Term Treatment with Terlipressin as a Bridge to Liver Transplantation," Disgestive Diseases and Sciences, Jun. 1996, pp. 1054-1056, vol. 41, No. 6.
Gerbes et al., "Terlipressin for Hepatorenal Syndrome: Continuous Infusion as an Alternative to IV Bonus Administration," Gastroenterology, 2009, pp. 1179-1189, vol. 137.
Ghosh et al., "Noradrenaline vs terlipressin in the treatment of type 2 hepatorenal syndrome: a randomized pilot study," Liver International, 2013, pp. 1187-1193.
Gluud et al., "Systematic Review of Randomized Trials on Vasoconstrictor Drugs for Hepatorenal Syndrome," Hepatology, Feb. 2010, pp. 576-584.
Gluud et al., "Terlipressin for hepatorenal syndrome (Review)," The Cochrane Collaboration, 2012, pp. 1-35, No. 9.
Gordon, M.D., Fredric D., "Ascites," Clin. Liver Dis., 2012, pp. 285-299, vol. 16.
Gow, M.D., Paul et al., "Outpatient Terlipressin Infusion for the Treatment of Refractory Ascites," The American Journal of Gastroenterology, Jul. 2016, pp. 1041-1042, vol. 111.
Huang, Y-Y et al., "Terlipressin Resolves Ascites of Cirrhotic Rats through Downregulation of Aquaproin 2," The Journal of International Medical Research, 2012, pp. 1735-1744, vol. 40.
Jarcuska et al., "Hepatorenal Syndrome Type 1 in Patients with Acute Alcoholic Hepatitis Treated with Continual Terlipressin Infusion in Combination with Albumin Plasmaexpansion," Hepatology, 2002, p. 256, vol. 36 (S1).
Jarcuska et al., "Hemodialysis in Hepatorenal Syndrome Type 1 in Alcoholic Liver Cirrhosis Treated by Continual Terlipressin Infusion in Combination with Albumin Plasmaexpansion," Hepatology, 2003, pp. 194-195, 2003, vol. 38 (S2).
Kalambokis et al., "Effects of somatostatin, terlipressin and somatostatin plus terlipressin on portal and systemic hemodynamics and renal sodium excretion in patients with cirrhosis," Journal of Gastroenterology and Hepatology, 2005, pp. 1075-1081, vol. 20.
Kalambokis et al., "Vasoconstrictor Therapy for Patients with Cirrhosis with Ascites but Without Hepatorenal Syndrome," Hepatology, 2008, p. 686, vol. 48, No. 2.
Kalambokis et al., "Effects of terlipressin on water excretion after oral water load test in nonazotemic cirrhotic patients with ascites without hyponatremia," Scandinavian Journal of Gastroenterology, 2010, pp. 1509-1515, vol. 45, No. 12.
Krag et al., "Terlipressin Improves Renal Function in Patients with Cirrhosis and Ascites Without Hepatorenal Syndrome," Hepatology, 2007, pp. 1863-1871, vol. 46.
Krag, Aleksander, "Efficacy and Safety of Terlipressin in Cirrhotic Patients and Variceal Bleeding or Hepatorenal Syndrome," Adv. Ther., 2008, pp. 1105-1140, vol. 25, No. 11.
Lange et al., "Continuous Versus Bolus Infusion of Terlipressin in Ovine Endotoxemia," Shock, 2007, 8 pages, vol. 28, No. 5.
Lenaerts et al., "Comparative pilot study of repeated large volume paracentesis vs the combination on clonidine-spironolactone in the treatment of cirrhosis-associated refractory ascites," Gastroenterol Clin Biol, 2005, pp. 1137-1142, vol. 29.
Martín-Llahí et al., "Terlipressin and Albumin vs Albumin in Patients With Cirrhosis and Hepatorenal Syndrome: a Randomized Study," Gastroenterology, 2008, pp. 1352-1359, vol. 134.

Morelli et al., "Continuous terlipressin versus vasopressin infusion in septic shock (TERLIVAP): a randomized, controlled pilot study," Critical Care, 2009, 14 pages, vol. 13.
Mulkay et al., "Long-term terlipressin administration improves renal function in cirrhotic patients with type 1 hepatorenal syndrome: a pilot study," Acta Gastro-Enterologica Belgica, Jan.-Mar. 2001, pp. 15-19, vol. 64.
Neri et al., "Terlipressin and Albumin in Patients with Cirrhosis and Type 1 Hepatorenal Syndrome," Dig. Dis. Sci., 2008, pp. 830-835, vol. 53.
Nilsson et al., "Pharmacokinetics of Terlipressin After Single I.V. Doses to Healthy Volunteers," Drugs Exptl Clin. Res., 1990, pp. 307-314, vol. XVI, No. 6.
Ortega et al., "Terlipressin Therapy With and Without Albumin for Patients With Hepatorenal Syndrome: Results of a Prospective, Nonrandomized Study," Hepatology, Oct. 2002, pp. 941-948, vol. 36.
Parry, Nicola, "Terlipressin and Albumin Combination Therapy Improves Renal Function in HRS-1," Peer-Reviewed Highlights from AASLD: The Liver Meeting, Dec. 2014, pp. 17-18.
Piano et al., "Continuous recurrence of type 1 hepatorenal syndrome and long-term treatment with terlipressin and albumin: A new exception to MELD score in the allocation system to liver transplantation?" Journal of Hepatology, 2011, pp. 491-496, vol. 55.
Robertson et al., "Continuous Outpatient Terlipressin Infusion for Hepatorenal Syndrome as a Bridge to Successful Liver Transplantation," Hepatology, 2014, 2 pages.
Rodriguez et al., "Treatment of Type 2 Hepatorenal Syndrome in Patients Awaiting Transplantation: Effects on Kidney Function and Transplantation Outcomes," Liver Transplantations, 2015, pp. 1347-1354, vol. 21.
Runyon, M.D., Bruce A., "Management of Adult Patients with Ascites Due to Cirrhosis: Update 2012," AASLD Practice Guideline, Hepatology, Feb. 2013, pp. 1-27.
Sagi et al., "Terlipressin therapy for reversal of type 1 hepatorenal syndrome: A meta-analysis of randomized controlled trials," Journal of Gastroenterology and Hepatology, 2010, pp. 1-6.
Saner et al., "Terlipressin plus hydroxyethyl starch infusion: an effective treatment for hepatorenal syndrome," European Journal of Gastroenterology & Hepatology, 2003, pp. 925-927, vol. 15.
Sanyal et al., "A Randomized, Prospective, Double-Blind, Placebo-Controlled Trial of Terlipressin for Type 1 Hepatorenal Syndrome," Gastroenterology, 2008, pp. 1360-1368, vol. 134.
Singh et al., "Midodrine in patients with cirrhosis and refractory or recurrent ascites: A randomized pilot study," Journal of Hepatology, 2012, pp. 348-354, vol. 56.
Singh et al., "Midodrine and Clonidine in Patients With Cirrhosis and Refractory or Recurrent Ascites: A Randomized Pilot Study," The American Journal of Gastroenterology, Apr. 2013, pp. 560-567, vol. 108.
Siqueira, M.D., Fabiolla et al., "Refractory Ascites: Pathogeneis, Clinical Impact, and Management," Gastroenterology & Hepatology, Sep. 2009, pp. 647-656, vol. 5, No. 9.
Solà et al., "Hyponatremia in Patients Treated With Terlipressin for Severe Gastrointestinal Bleeding Due to Portal Hypertension," Hepatology, 2010, pp. 1783-1790, vol. 52.
Solanki et al., "Beneficial effects of terlipressin in hepatorenal syndrome: A prospective, randomized placebo-controlled clinical trial," Journal of Gastroenterology and Hepatology, 2003, pp. 152-156, vol. 18.
Tandon et al., "The effect of 1 month of therapy with midodrine, octreotide-LAR and albumin in refractory ascites: a pilot study," Liver International, 2009, pp. 169-174.
Therapondos et al., "Systemic, portal and renal effects of terlipressin in patients with cirrhotic ascites: Pilot Study," Journal of Gastroenterology and Hepatology, 2004, pp. 73-77, vol. 19.
Vasudevan et al., "Efficacy of outpatient continuous terlipressin infusions for hepatorenal syndrome," Hepatology, 2015, 5 pages.
Wong, Florence, "Management of ascites in cirrhosis," Journal of Gastroenterology and Hepatology, 2012, pp. 11-20, vol. 27.

\* cited by examiner

TREATMENT OF ASCITES

RELATED APPLICATIONS

This application claims the benefit of U.S. Provisional patent application 62/321,558, filed Apr. 12, 2016, U.S. Provisional patent application 62/267,510, filed Dec. 15, 2015, and U.S. Provisional patent application 62/186,638, filed Jun. 30, 2015, each of which is incorporated by reference herein their entirety

FIELD

The disclosure is directed to a method for treating ascites patients by administering the peptide drug terlipressin.

BACKGROUND

Ascites is a frequent and life-threatening complication of advanced liver cirrhosis with an expected 40% mortality rate within two years of diagnosis. To date the US FDA has not approved any therapies specifically to treat ascites, although a few drugs (e.g., diuretics) are being used off-label with limited and temporary efficacy. Studies have shown that intravenous (IV) injections of terlipressin every 4 to 6 hours in hospitalized patients with type 1 hepatorenal syndrome (HRS) can save their lives. FIRS is the beginning of renal failure and frequently occurs in patients with ascites that has become refractory to treatment with diuretics. Additionally, investigational studies have shown that IV injections of terlipressin every 4 to 6 hours in combination with diuretics may resolve refractory ascites in hospitalized patients and decrease the need for large volume paracentesis (ascites fluid withdrawal by needle). However these intermittent high-dose IV injections (typically 1 or 2 mg in a single dose) carry a high risk of side-effects. More recent studies with hospitalized HRS patients indicate that a continuous infusion of terlipressin can achieve similar efficacy to intermittent injections with a much better safety profile. However to date there have been no published studies of using a continuous low-dose infusion terlipressin to manage ascites in non-hospitalized patients with cirrhosis.

Accordingly, the inventors have identified a need in the art for a method to treat ascites patients on an outpatient basis and potentially avoid or delay the need for hospitalization due to HRS or other life-threatening complications.

SUMMARY

In one aspect, the disclosure is directed to a method for treating a patient diagnosed with ascites due to liver cirrhosis. The method including administering terlipressin or salt thereof as a continuous infusion. The condition of the patient may not have progressed to HRS.

In another aspect, the disclosure is directed to a method for reducing the volume of ascitic fluid during a paracentesis procedure in an ascites patient. The method includes administering terlipressin or salt thereof as a continuous infusion.

In yet another aspect, the disclosure is directed to a method for reducing the number of monthly paracentesis procedures in an ascites patient. The method includes administering terlipressin or salt thereof as a continuous infusion.

Still further, the disclosure is directed to a method for improving renal function in an ascites patient. The method includes administering terlipressin or salt thereof as a continuous infusion. In various aspects, the improvement in renal function includes one or more of the following: a reduction in serum creatinine concentration, an increase in plasma sodium concentration, an increase in urinary sodium excretion, and a decrease in urea concentration in serum.

The disclosure is also directed to a method for correcting hyponatremia in an ascites patient. The method includes administering to the patient terlipressin or salt thereof as a continuous infusion.

In a further aspect, the disclosure is directed to a method for improving the health status of the ascites patient with liver cirrhosis due to hepatitis C. The method includes method comprising administering a hepatitis C antiviral medication in combination with administering terlipressin or salt thereof as a continuous infusion.

In another aspect, the disclosure is directed to a method of improving the Model for End-Stage Liver Disease (MELD) score of an ascites patient. The method includes administering terlipressin or salt thereof with a continuous infusion.

In each of the aspects of the invention, the condition of the patient may not have progressed to HRS. Also, the terlipressin dose may range from about 1.0 mg to about 12.0 mg per day, and the terlipressin dose may be escalated over the course of the therapy. In addition, the terlipressin may be administered for a time period of about 1 day to about 12 months. Further, the continuous terlipressin may be administered with an ambulatory infusion pump.

DESCRIPTION

Terlipressin is a synthetic vasopressin that is approved in many countries outside of the United States to treat the life-threatening complications of cirrhosis, including hepatorenal syndrome (HRS) and esophageal bleeding (EVB). Its use is limited to the hospital setting due to its short half-life (26 minutes) (Nilsson, et al., 1990), necessitating its administration as an intravenous bolus usually every 4 to 6 hours. Additionally, terlipressin can cause side effects in up to 40% of patients. Severe side effects—including myocardial infarction, arrhythmia and intestinal infarction—can require discontinuation of treatment in up to 10% of the patients (Angeli, 2011). Indeed, due to the rapid vasoconstrictor properties, IV bolus dosed terlipressin must be used with caution in patients with severe asthma, severe hypertension, advanced atherosclerosis, cardiac dysrhythmias, and coronary insufficiency.

In one aspect, the disclosure is directed to the administering terlipressin or a salt thereof for the treatment of patients suffering from ascites due to, for example, advanced liver cirrhosis. These patients are typically non-hospitalized (or ambulatory) and may include patients whose condition has not progressed to type 2 HRS (ambulatory HRS patients) or type 1 HRS (requiring hospitalization). Treatment includes a continuous infusion of terlipressin by means of a pump device, typically a portable ambulatory pump, for a period of several hours, lasting up to days, weeks, or months. The treatment is effective at reducing or resolving ascites disease on, for most patients, an outpatient basis.

Patients with cirrhosis exhibiting type 1 hepatorenal syndrome (HRS-1) have been safely treated with terlipressin administered continuously. Dosage ranged from 2.0-12.0 mg per 24 hours (Angeli, et al., 2009: 2-12 mg/24 h; Gerbes, 2009: starting dose 3 mg/day; Robertson, et al., 2014: 3 mg/day; Ding, 2013: 4 mg/day; Cavallin 2015: 3-12 mg/day). However, none of these studies have either evaluated or reported an effect of terlipressin infusion on ascites burden or the effect of continuous infusion terlipressin on patients whose condition have not progressed to HRS.

Ambulatory pumps are commonly used to infuse parenteral drugs directly into the bloodstream via catheters to increase efficacy and/or decrease toxicity. This has been found to be safer than some approved terlipressin drug therapy that require the administration of terlipressin to hospitalized hepatorenal syndrome (HRS) patients and esophageal bleed (EVB) patients using slow bolus IV injections. Accordingly, in one aspect of the disclosure, terlipressin is administered continuously by a pump at a dosage rate of about 0.5 mg to about 20 mg every 24 hours, more particularly for example, about 1 mg to about 12 mg every 24 hours, more particularly for example, about 5 to about 15 mg every 24 hours, or for instance, about 1, 2, 3, 4, 5, 6, 7, 8, 9, 10, 11, 12, 13, 14, 15, 16, 17, 18, 19, or 20 mg every 24 hours. Administration can continue for, typically, at least about one day and may continue for about 12 months or longer as necessary to bridge a patient until a transplant is available. For example, the administration can continue for about 1 day, 2 days, 3 days, 4 days, 5 days, 6 days, one week, two weeks, three weeks, one month, two months, three months, six months, 9 months or twelve months. In some instances, the dose of terlipressin escalates over the course of the therapy. For example, patients may begin therapy at 2 mg/day, and be increased to 3 mg/day or up to 12 mg/day over the course of treatment.

Accordingly, in various aspects, the disclosure is directed to a method for treating a patient diagnosed with ascites due to liver cirrhosis. The method can improve renal function in an ascites patient and reduce the volume of ascitic fluid during paracentesis procedure in the patient. Still further, the method can be used for reducing the risk of spontaneous bacterial peritonitis, improving the Model for End-Stage Liver Disease (MELD) score of an ascites patient and/or correcting hyponatremia in an ascites patient. In another aspect, the method disclosed herein can be used in combination with hepatitis C antiviral medications to improve the health status of the ascites patient with liver cirrhosis due to hepatitis C. In each case terlipressin or salt thereof is administered with a continuous infusion pump. In each of these aspects, the patient's ascites condition may not have progressed to hepatorenal syndrome.

In addition, the determination of the presence, progression, or improvement of disease can be determined by measuring one or more of the following: serum creatinine concentration, plasma sodium concentration, urinary sodium excretion, and urea concentration in serum. For example, an improvement in renal function that indicates an improvement in disease condition includes one or more of the following: a reduction in serum creatinine concentration, an increase in plasma sodium concentration, an increase in urinary sodium excretion, a decrease in urea concentration in serum of disease.

The use of ambulatory pump delivery of continuous infusion of terlipressin would avoid the need for patient hospitalization and make such therapy available to the vast majority of ascites patients who have not yet been hospitalized for severe complications that often follow advanced ascites, such as post-paracentesis circulatory dysfunction, HRS, EVB, hepatic encephalopathy, spontaneous bacterial peritonitis and other life-threatening conditions.

EXAMPLES

The following are provided for exemplification purposes only and are not intended to limit the scope of the disclosure described in broad terms above.

Example 1

Treatment of Ascites with Continuous Infusion Pump Terlipressin Therapy 15 subjects that are to be confirmed to have ascites, but not type 1 or type 2 HRS, due to liver cirrhosis will be administered continuous low dose (escalating from 2.0 to 3.0 mg per 24 hours) terlipressin via ambulatory infusion pump. These patients are expected to experience a decrease the severity of ascites and the accumulation of ascites fluid over the course of treatment ranging from 1 day to 28 days. This method is also expected to reduce the number of paracentesis procedures required to remove ascitic fluid over a 28-day period, compared to the 28-day period prior to treatment inception, and some patients should avoid paracentesis altogether. Additionally the average amount of fluid withdrawn after beginning continuous infusion pump terlipressin therapy should be significantly less than prior to the start of treatment. Furthermore the improvement in patient health status can be achieved safely with no serious side effects. Accordingly, continuous infusion pump (CIP) terlipressin represents a potentially life-saving solution for these seriously ill patients who are still ambulatory (have not yet been administered to the hospital for treatment) and have not developed type 1 or type 2 HRS.

Example 2

Treatment of Ascites with Continuous Infusion Pump Terlipressin Therapy

Six FIRS patients treated with continuous infusion terlipressin were evaluated for improvement in acsites. All six patients had diuretic intractable or refractory ascites (5 of 6 with hyponatremia). The patients were evaluated for the following parameters before, during and after treatment: number of paracentesis procedures per month, volume of ascites removed, weight, serum sodium, urinary sodium excretion, serum creatinine, serum urea, and whether diuretics were included in the treatment regimen. None of the six patients had a complete set of data for all parameters. The effect of continuous infusion terlipressin on each parameter is presented in Tables 1-7.

Reduction in frequency of paracentesis and fluid volume during therapy

The average number of monthly paracentesis procedures decreased from three prior to initiation of continuous infusion therapy to two during therapy, and the average monthly ascites fluid volume removed was reduced by 55%.

TABLE 1

| Patient # M/F | Max. Dose (mg/day) | Duration (days) | Paracenteses/Month | | | Volume Fluid Removed/Month (L) | | |
|---|---|---|---|---|---|---|---|---|
| | | | Before | During | % Change | Before | During | % Change |
| 1 M | 12 | 63 | 1 | 0 | −100% | — | — | — |
| 2 F | 12 | 195 | 8 | 6 | −25% | 80 | 42 | −48% |
| 3 M | 3 | 10 | 4 | 2 | −50% | 40 | 14 | −65% |
| 4 M | 10 | 11 | 2 | 3 | 50% | 14 | 9 | −36% |

TABLE 1-continued

|  |  |  | Paracenteses/Month | | | Volume Fluid Removed/Month (L) | | |
| --- | --- | --- | --- | --- | --- | --- | --- | --- |
| Patient # M/F | Max. Dose (mg/day) | Duration (days) | Before | During | % Change | Before | During | % Change |
| 5 F | 3 | 22 | 3 | 2 | −33% | 21 | 6 | −71% |
| 6 F | 2 | 12 | 1 | 0 | −100% | 2 | 0 | −100% |
| Average (excludes patient #1): | | | 3 | 2 | −32% | 31 | 14 | −55% |

"—" indicates missing data

Reduction in Body Weight During Therapy

Average body weight per patient, a proxy for ascitic fluid accumulation in the abdominal cavity, decreased by 11% or 9 kg (~19.8 lbs).

TABLE 2

|  | Max. Terli. | | Body Weight (kg) | | | |
| --- | --- | --- | --- | --- | --- | --- |
| Patient # M/F | Dose (mg/day) | Duration (days) | Before | During | % Change | After |
| 1 M | 12 | 63 | 83 | 74 | −11% | 74 |
| 2 F | 12 | 195 | 64 | 71 | 11% | — |
| 3 M | 3 | 10 | 128 | 99 | −23% | 128 |
| 4 M | 10 | 11 | 60 | — | — | — |
| 5 F | 3 | 22 | 71 | 64 | −10% | 77 |
| 6 F | 2 | 12 | 64 | 55 | −14% | 68 |
| Average (excludes patient #4): | | | 82 | 73 | −11% | 87 |

"—" indicates missing data

Requirement for Diuretics for Effect on as Cites

During treatment, improvement of ascites was seen without diuretics in four of six patients.

TABLE 3

|  |  | Treatment | | % Change | | |
| --- | --- | --- | --- | --- | --- | --- |
| Patient # M/F | Max. Terli. Dose (mg/day) | Diuretics Before | Diuretics During | Paracentesis per Month | Volume Fluid Removed | Body Weight |
| 1 M | 12 | A | A | −100% | — | −11% |
| 2 F | 12 | A | None | −25% | −48% | 11% |
| 3 M | 3 | F + A | None | −50% | −65% | −23% |
| 4 M | 10 | F + A | None | 50% | −36% | — |
| 5 F | 3 | A | None | −33% | −71% | −10% |
| 6 F | 2 | F + A | F + A | −100% | −100% | −14% |
| | | | Average: | −32% | −55% | −11% |

F = furosemide;
A = anti-aldosteronic drug.
"—" indicates missing data.

Increase in Urinary Sodium Excretion During Therapy

The observed improvement in ascites and renal function was further supported by a substantial increase in excretion of sodium into the urine. The average urinary sodium increased from 7 to 127 mEq/24 h in three of sis patients with data recorded before and after starting continuous infusion terlipressin therapy.

TABLE 4

|  | Max. Terli. | | Urinary Na over 24 hours (mEq/24 hr) | | |
| --- | --- | --- | --- | --- | --- |
| Patient # M/F | Dose (mg/day) | Duration (days) | Before | During | % Change |
| 1 M | 12 | 63 | 5 | 46 | 820% |
| 2 F | 12 | 195 | — | 301 | — |

TABLE 4-continued

|  | Max. Terli. | | Urinary Na over 24 hours (mEq/24 hr) | | |
| --- | --- | --- | --- | --- | --- |
| Patient # M/F | Dose (mg/day) | Duration (days) | Before | During | % Change |
| 3 M | 3 | 10 | — | — | — |
| 4 M | 10 | 11 | 1 | 20 | 1900% |
| 5 F | 3 | 22 | — | 33/140 | — |
| 6 F | 2 | 12 | 16 | 315 | 1869% |
| | | | 7 | 127 | 1632% |

Average (excludes patients #2, #3, #5):
"—" indicates missing data

Improvement in Plasma Sodium

Treatment with continuous infusion terlipressin corrected severe hyponatremia in two patients: Plasma Na increased by 15% in patient #4 and by 19% in patient #6. Importantly, after the cessation of therapy, plasma sodium remained normal in patient #6 (data "after therapy" available for one of the two patients).

TABLE 5

|  | Max. Terli. | | Plasma Sodium (mEq/L) | | | |
| --- | --- | --- | --- | --- | --- | --- |
| Patient # M/F | Dose (mg/day) | Duration (days) | Before | During | % Change | After |
| 1 M | 12 | 63 | 140 | 137 | −2% | — |
| 2 F | 12 | 195 | 125 | 128 | 2% | — |
| 3 M | 3 | 10 | 133 | 136 | 2% | 140 |
| 4 M | 10 | 11 | 123 | 141 | 15% | — |
| S F | 3 | 22 | 131 | 128 | −2% | — |
| 6 F | 2 | 12 | 118 | 140 | 19% | 131 |
| | | Average: | 128 | 135 | 5% | 136 |

"—" indicates missing data

Reduction in Blood Urea During Treatment

The concentration of urea in patients' blood serum decreased in all patients by an overall average of 45%. This increase in urea clearance is indicative of improved renal function.

TABLE 6

| Patient # M/F | Max. Terli. Dose (mg/day) | Duration (days) | Serum Urea (mmol/L) | | | |
|---|---|---|---|---|---|---|
| | | | Before | During | % Change | After |
| 1 M | 12 | 63 | 31.1 | 8.8 | −72% | — |
| 2 F | 12 | 195 | 36.6 | 23.2 | −37% | — |
| 3 M | 3 | 10 | 17.0 | 9.1 | −46% | 10.8 |
| 4 M | 10 | 11 | 51.8 | 37.3 | −28% | — |
| 5 F | 3 | 22 | 6.4 | 5.3 | −17% | 10.5 |
| 6 F | 2 | 12 | 20.4 | 6.6 | −68% | 10.0 |
| | | Average: | 27.2 | 15.1 | −45% | 10.4 |

"—" indicates missing data

Reduction in Serum Creatinine

Levels of the metabolic waste product serum creatinine are indicative of renal health. An average decrease of 47% was seen in serum creatinine levels for the treated group of patients. This was consistent with the decrease in serum urea and indicates improved renal function, contributing to a decrease in ascites severity.

TABLE 7

| Patient # M/F | Max. Terli. Dose (mg/day) | Duration (days) | Serum Creatinine (mmol/L) | | | |
|---|---|---|---|---|---|---|
| | | | Before | During | % Change | After |
| 1 M | 12 | 63 | 248 | 189 | −24% | — |
| 2 F | 12 | 195 | 383 | 208 | −46% | — |
| 3 M | 3 | 10 | 233 | 116 | −50% | 122 |
| 4 M | 10 | 11 | 319 | 104 | −67% | — |
| 5 F | 3 | 22 | 68 | 55 | −19% | 55 |
| 6 F | 2 | 12 | 195 | 90 | −54% | 137 |
| | | Average: | 241 | 127 | −47% | 105 |

"—" indicates missing data

All references cited in this disclosure are incorporated herein by reference.

Nilsson, G. et al., 1990. Nilsson G, Lindblom P, OhlPharmacokinetics of Terlipressin After Single i.v. Doses to Healthy Volunteers. Drugs Under Experimental and Clinical Research, Volume 16, pp. 307-314.

Angeli, P., 2011. Terlipressin for Hepatorenal Syndrome: Novel Strategies and Future Perspectives. Frontiers of Gastrointestinal Research, Volume 28, pp. 189-197.

Angeli, P. et al., 2009. Terlipressin Given as Continous Intravenous Infusion Versus Terlipressin Given as Intravenous Boluses in the Treatment of Type 1 Hepatorenal Syndrome (HRS) in Patients with Cirrhosis. Journal of Hepatology, 50 (Supplement 1), p. S73.

Gerbes A L, Huber E, Gülberg V. 2009 Terlipressin for hepatorenal syndrome: continuous infusion as an alternative to i.v. bolus administration. 2009 Gastroenterology. 137(3): 1179; author reply 1179-81

Ding, C. et al., 2013. Hemodynamic effects of continuous versus bolus infusion of terlipressin for portal hypertension: A randomized comparison. Journal of Gastroenterology and Hepatology, 28(7), pp. 1242-1246.

Robertson, M. et al., 2014. Continuous outpatient terlipressin infusion for hepatorenal syndrome as a bridge to successful liver transplantation. Hepatology Mar 2014. Hepatology, Volume March, pp. 1-2.

Cavallin M, et. al., 2015 Terlipressin Plus Albumin Versus Midodrine and Octreotide Plus Albumin in the Treatment of Hepatorenal Syndrome: A Randomized Trial. Hepatology, 2015 (in press)

Fimiani, B. et al., 2011. The Use of Terlipressin in Cirrhotic Patients with Refractory Ascites and Normal Renal Function: A Multicentric Study. European Journal of Internal Medicine, Volume 22, pp. 587-590.

Krag, A. et al., 2007. Telipressin Improves Renal Function in Patients with Cirrhosis and Ascites Without Hepatorenal Syndrome. Hepatology, 46(6), pp. 1863-1871.

Although various specific embodiments of the present disclosure have been described herein, it is to be understood that the disclosure is not limited to those precise embodiments and that various changes or modifications can be affected therein by one skilled in the art without departing from the scope and spirit of the disclosure.

What is claimed is:

1. A method for treating a patient diagnosed with ascites due to liver cirrhosis, the method comprising administering terlipressin or salt thereof as a continuous infusion dose of about 1.0 mg to about 12.0 mg per day to the patient for about one day to about 12 months.

2. The method of claim 1, wherein the continuous terlipressin is administered for about one day to about six months.

3. The method of claim 1, wherein the continuous terlipressin is administered with an ambulatory infusion pump.

4. The method of claim 1, wherein the patient has not progressed to hepatorenal syndrome (HRS).

5. The method of claim 1, wherein the administration of terlipressin is provided on an out-patient basis.

6. The method of claim 1, wherein the administered dose of terlipressin escalates over the about one day to about 12 months.

7. A method for reducing the accumulation of ascitic fluid in the abdominal cavity in an ambulatory ascites patient, the method comprising administering to the patient terlipressin or salt thereof as a continuous infusion dose of about 1.0 mg to about 12.0 mg per day for about one day to about twelve months with an ambulatory infusion pump.

8. The method of claim 7, wherein the terlipressin is administered for about one day to about six months.

9. The method of claim 7, wherein the patient has not progressed to hepatorenal syndrome (HRS).

10. The method of claim 7, wherein the administration is provided on an out-patient basis.

11. The method of claim 7, wherein the administered dose of terlipressin escalates over the about one day to about 12 months.

12. The method of claim 1, wherein patient has not progressed to FIRS type 1.

13. The method of claim 12, where the patient is not hospitalized.

14. The method of claim 7, wherein the patient has not progressed to HRS type 1.

* * * * *

UNITED STATES PATENT AND TRADEMARK OFFICE
CERTIFICATE OF CORRECTION

PATENT NO. : 9,655,945 B2
APPLICATION NO. : 15/198050
DATED : May 23, 2017
INVENTOR(S) : Paolo Angeli et al.

Page 1 of 1

It is certified that error appears in the above-identified patent and that said Letters Patent is hereby corrected as shown below:

In the Specification

In the Background
In Column 1, Line 26, replace "FIRS" with "HRS"

In the Examples
In Column 4, Line 38, replace "FIRS" with "HRS"
In Column 5, Line 32, replace "as Cites" with "Ascites"

In the Claims

In Column 8, Line 58, replace "FIRS" with "HRS"

Signed and Sealed this
Fifteenth Day of August, 2017

Joseph Matal
*Performing the Functions and Duties of the
Under Secretary of Commerce for Intellectual Property and
Director of the United States Patent and Trademark Office*

(12) INTER PARTES REVIEW CERTIFICATE (2153rd)
United States Patent
Angeli et al.

(10) Number: US 9,655,945 K1
(45) Certificate Issued: Jun. 23, 2021

(54) TREATMENT OF ASCITES

(71) Applicants: Paolo Angeli; Penelope Markham; Jonathan Adams

(72) Inventors: Paolo Angeli; Penelope Markham; Jonathan Adams

(73) Assignee: UNIVERSITA DEGLI STUDI DI PADOVA

Trial Number:

IPR2018-00974 filed Apr. 27, 2018

Inter Partes Review Certificate for:

Patent No.: 9,655,945
Issued: May 23, 2017
Appl. No.: 15/198,050
Filed: Jun. 30, 2016

The results of IPR2018-00974 are reflected in this inter partes review certificate under 35 U.S.C. 318(b).

INTER PARTES REVIEW CERTIFICATE
U.S. Patent 9,655,945 K1
Trial No. IPR2018-00974
Certificate Issued Jun. 23, 2021

AS A RESULT OF THE INTER PARTES REVIEW PROCEEDING, IT HAS BEEN DETERMINED THAT:

Claims 1-14 are cancelled.

\* \* \* \* \*